(12) United States Patent
Painchaud et al.

(10) Patent No.: US 10,220,988 B2
(45) Date of Patent: Mar. 5, 2019

(54) DEVICE FOR DISPENSING A LIQUID IN THE FORM OF DROPS

(75) Inventors: Gaetan Painchaud, Francheville (FR);
Sylvain Lanzi, Chirens (FR); Xavier Julia, Villefontaine (FR); Guillaume Grevin, L'Isle d'Abeau (FR)

(73) Assignee: Nemera La Verpillière (FR)

( * ) Notice: Subject to any disclaimer, the term of this patent is extended or adjusted under 35 U.S.C. 154(b) by 927 days.

(21) Appl. No.: 12/891,366

(22) Filed: Sep. 27, 2010

(65) Prior Publication Data

US 2011/0155770 A1   Jun. 30, 2011

Related U.S. Application Data

(63) Continuation of application No. PCT/FR2009/000356, filed on Mar. 27, 2009.

(30) Foreign Application Priority Data

Mar. 27, 2008 (FR) ........................ 08 51994
Oct. 15, 2008 (FR) ........................ 08 05717

(51) Int. Cl.
*B65D 47/18* (2006.01)
*B65D 47/20* (2006.01)
*A61J 1/14* (2006.01)
*A61F 9/00* (2006.01)

(52) U.S. Cl.
CPC ............ *B65D 47/18* (2013.01); *A61J 1/1425* (2015.05); *B65D 47/205* (2013.01); *B65D 47/2081* (2013.01); *A61F 9/0008* (2013.01); *A61J 1/1468* (2015.05)

(58) Field of Classification Search
USPC ....... 222/420, 209, 212, 213, 498, 499, 422, 222/511, 513, 514, 518, 494, 495, 496
See application file for complete search history.

(56) References Cited

U.S. PATENT DOCUMENTS 2,817,462 A * 12/1957 Lipinski .................... 222/212
2,987,223 A *  6/1961 Armour ..................... 222/207
5,025,957 A *  6/1991 Ranalletta et al. ...... 222/189.09
5,154,325 A * 10/1992 Ryder et al. ............. 222/189.06
(Continued)

FOREIGN PATENT DOCUMENTS

DE   102006012898 A1   9/2007
EP       0362911 A1   4/1990
(Continued)

OTHER PUBLICATIONS

French Search Report; Application No. FR 0851994; dated Dec. 17, 2008; 6 pages.
(Continued)

*Primary Examiner* — Patrick M Buechner
*Assistant Examiner* — Michael J Melaragno
(74) *Attorney, Agent, or Firm* — St. Onge Steward Johnston & Reens, LLC

(57) ABSTRACT

The device makes it possible to dispense predetermined metered quantities of liquid. It includes a sealing member that can take up a liquid release position, allowing liquid to flow out of the device, and a non-return position preventing liquid from flowing back into the device. The sealing member is provided with metering means for metering out the liquid to be dispensed.

12 Claims, 2 Drawing Sheets

(56) References Cited

U.S. PATENT DOCUMENTS

| | | | |
|---|---|---|---|
| 5,183,184 A * | 2/1993 | Ranalletta et al. | 222/189.09 |
| 5,219,101 A * | 6/1993 | Matkovich et al. | 222/189.06 |
| 5,226,568 A | 7/1993 | Newton et al. | |
| 5,310,094 A | 5/1994 | Martinez et al. | |
| 5,320,254 A | 6/1994 | Ranalletta | |
| 5,431,310 A * | 7/1995 | Kanner et al. | 222/212 |
| 6,076,709 A * | 6/2000 | Wilner | 222/212 |
| 6,250,509 B1 | 6/2001 | Fuchs | |
| 6,616,019 B2 * | 9/2003 | D'Alessio et al. | 222/566 |
| 6,672,479 B2 | 1/2004 | Shiraishi et al. | |
| 6,974,053 B2 | 12/2005 | Lautre et al. | |
| 7,677,417 B2 * | 3/2010 | Leiner et al. | 222/212 |
| 2002/0017294 A1 | 2/2002 | Py | |
| 2003/0190079 A1 | 10/2003 | Penain et al. | |
| 2004/0134940 A1 * | 7/2004 | Hearld et al. | 222/481.5 |
| 2005/0173468 A1 | 8/2005 | Matsumoto et al. | |
| 2006/0180613 A1 | 8/2006 | Manesis | |
| 2006/0197042 A1 | 9/2006 | Kneer | |
| 2006/0261097 A1 * | 11/2006 | Bailey | 222/494 |
| 2006/0261098 A1 * | 11/2006 | Nilsson | 222/496 |
| 2007/0210114 A1 | 9/2007 | Stadelhofer et al. | |
| 2008/0019863 A1 * | 1/2008 | Kis et al. | 422/20 |

FOREIGN PATENT DOCUMENTS

| | | | | |
|---|---|---|---|---|
| EP | 0985454 | A2 | 3/2000 | |
| EP | 1561699 | A1 | 8/2005 | |
| EP | 1453738 | B1 | 7/2007 | |
| JP | H02139347 | A | 5/1990 | |
| JP | 7223662 | A | 8/1995 | |
| JP | 2543816 | B2 | 10/1996 | |
| JP | 2001240088 | A | 9/2001 | |
| JP | 2002513665 | A | 5/2002 | |
| JP | 2002263166 | A | 9/2002 | |
| JP | 2004001829 | A | 1/2004 | |
| JP | 2005219780 | A | 8/2005 | |
| WO | 03050010 | A2 | 6/2003 | |
| WO | 2004067400 | A1 | 8/2004 | |
| WO | 2004069679 | A1 | 8/2004 | |
| WO | 2006043295 | A1 | 4/2006 | |
| WO | 2006119315 | A2 | 11/2006 | |
| WO | WO 2006119315 | A2 * | 11/2006 | B65D 47/06 |

OTHER PUBLICATIONS

International Preliminary Report on Patentability and Written Opinion of the International Searching Authority; PCT/FR2009/000356; dated Nov. 2, 2010; 5 pages.

International Search Report; PCT/FR2009/000356; dated Sep. 14, 2009; 2 pages.

Notice of Reasons for Rejections Application No. 2011-501268 dated Jan. 14, 2014 5 pages.

Advisory Action from Japan Application No. 2011-501268 dated Nov. 25, 2014 6 pages.

* cited by examiner

DEVICE FOR DISPENSING A LIQUID IN THE FORM OF DROPS

CROSS-REFERENCE TO RELATED APPLICATIONS

The present application is a continuation of pending International patent application PCT/FR2009/000356 filed Mar. 27, 2009, which designates the United States and claims priority from French patent applications FR 0851994 filed Mar. 27, 2008 and FR 0805717 filed Oct. 15, 2008, the content of which is incorporated herein by reference.

FIELD OF THE INVENTION

The present invention relates to the technical field of dispensing predetermined metered quantities or "doses". More precisely, but not exclusively, the present invention relates to dispensing ophthalmic liquid such as collyrium or eyewash in the form of drops.

BACKGROUND OF THE INVENTION

State-of-the art devices are already known that make it possible to implement such dispensing in the form of drops. Generally, in order to form the delivered drops, the top portion of the dispensing head of the device has a shape of volume making it possible to define a drop.

SUMMARY OF THE INVENTION

An object of the present invention is to propose a device for dispensing predetermined metered quantities of liquid while also improving the sterility of the dispensed liquid.

To this end, the invention provides a device for dispensing predetermined metered quantities of liquid, which device includes a sealing member that can take up a liquid release position, allowing liquid to flow out of the device, and a non-return position preventing liquid from flowing back into the device, wherein the sealing member is provided with metering means for metering out the liquid to be dispensed.

Generally, the predetermined metered quantities of liquid are drops of liquid. It should also be noted that the non-return or position is equivalent to a liquid-blocking position.

By means of this provision, the means for metering out the liquid are provided directly by the sealing member, so that the liquid that is released by the sealing member in the release position, and that has just left the "sealed" zone of the device, is received directly in the metering means, without flowing through other parts. The risks of liquid penetrating into other portions of the device after being released by the sealing member are thus reduced. Indeed, when the metering means are provided on a part other than the sealing member, e.g. the outer casing of the dispensing end-piece of the device, the liquid can penetrate into other parts of the device while it is flowing between the sealing member and the metering means. Such penetration of liquid into undesired zones is a source of contamination, in particular through development of bacteria. Otherwise, in order to avoid such a risk, it is necessary to provide specific means for procuring sealing.

In addition, incorporating the metering means into the sealing member makes it easier to reduce any "dead volume" that might contain contaminated liquid. Such dead volume corresponds to the volume situated between the sealed zone (delimited in particular by the container and by the sealing member) and the metering means for metering out the drops. Since the metering means are on the sealing member, they are closer to the sealed zone, thereby keeping dead volume small. Furthermore, the sealing member can be made in such a manner that it fits as snugly as possible against the parts so as to achieve a further reduction in the dead volume. In addition, since the sealing member is generally made in part or entirely of a flexible material, it is easier to reduce the spaces so that it fits snugly against the parts than when the dead volume is defined by rigid parts.

The invention may also have one or more of the following characteristics.

The device includes bearing means for bearing against the sealing member, in register with a recessed zone, serving to deform the sealing member by bending deformation so that it takes up its non-return position.

The sealing member is flexible at least in part, and the device includes bearing means for bearing against the sealing member, serving to deform the flexible portion of the sealing member by compression deformation so that it takes up its non-return position. The flexible portion may be made of an elastomer material or of a material sufficiently flexible for procuring the sealing.

The metering means are means for forming drops of liquid.

The device includes a liquid-passing channel opening out into the drop-forming means and the drop-forming means comprise a flared shape that flares from said channel. This flared shape makes it possible to avoid jets of liquid being sprayed out.

The flared shape opens out into a substantially cylindrical shape. This cylindrical shape makes it possible to calibrate the drops that are formed.

The sealing member is an elastomer element that is made entirely of elastomer. However, the member may also be implemented differently, in particular by being made of a plastics material that is sufficiently flexible.

The sealing member comprises an elastomer portion and a rigid portion, said portions being constrained to move with each other. The presence of the rigid portion makes it possible for said rigid portion to receive any stresses exerted on the sealing member, while avoiding deforming the elastomer portion that thus procures sealing that is more constant over time.

The metering means are formed in the rigid portion.

The portion of the sealing member that is provided with the metering means is disposed in the immediate vicinity of an orifice for releasing liquid from the device.

BRIEF DESCRIPTION OF THE DRAWINGS

The invention can be better understood on reading the following description given merely by way of example, and with reference to the accompanying drawings, in which.

DETAILED DESCRIPTION OF THE INVENTION

Figure 2:
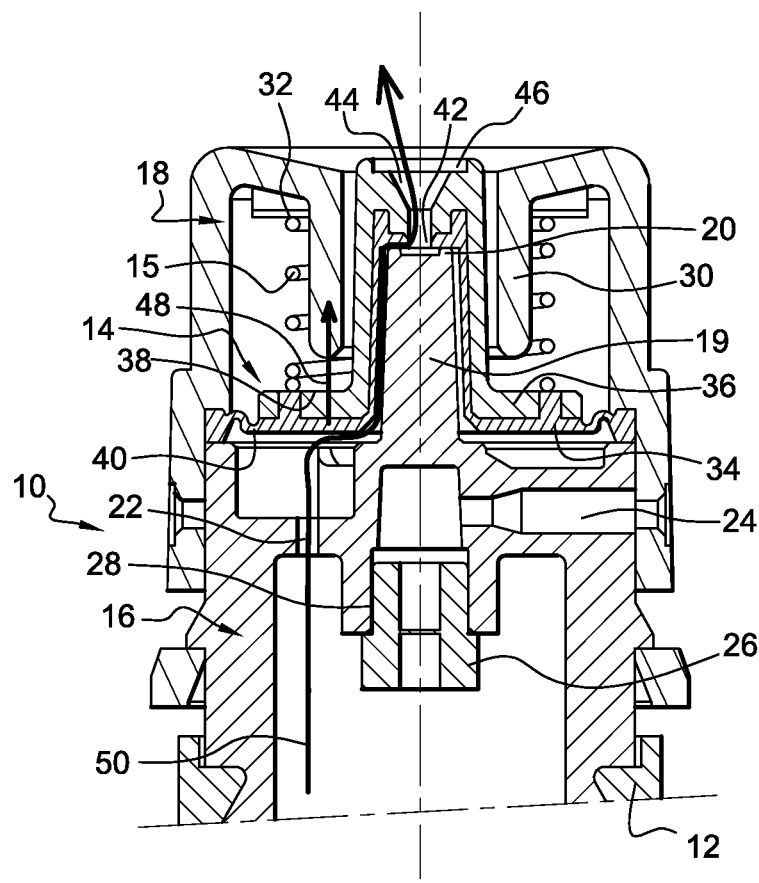
FIG. 2 is a view in longitudinal section showing an example of a device as shown diagrammatically in FIG. 1.
Figure 3:
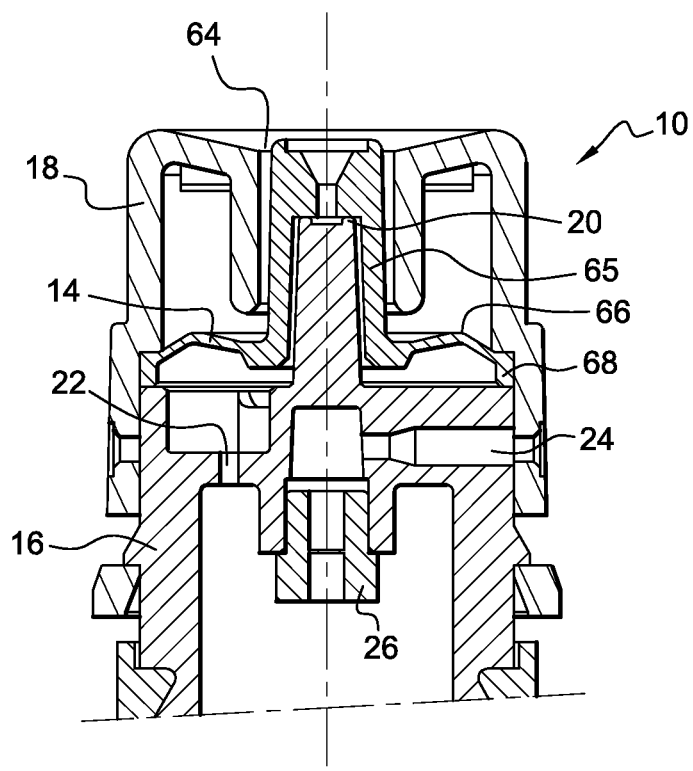
FIG. 3 is a view analogous to FIG. 2, showing a variant of the example of FIG. 2.

A liquid dispenser device comprises an end-piece 10, an example of which is shown in FIGS. 2 and 3, designed to be mounted on a container made of a plastics material and containing the liquid to be dispensed. The device makes it possible to dispense predetermined metered quantities of liquid, and more particular drops of liquid, for eye, nose, or mouth use, e.g. drops of collyrium or eyewash for the eyes. The end-piece 10 is mounted on a container 12, and more precisely on the neck 12 of the container, said container being designed to be squeezed by the user for the purpose of causing the liquid to flow out. In this example, the container 12 is made of a plastics material and is designed to be squeezed by the user to cause the liquid to flow out. It is possible to use other types of container, in particular containers made of glass or of metal, it being possible for the user to release the liquid by action other than by squeezing it, e.g. by pressing on an element for activating a pump.

Figure 1:
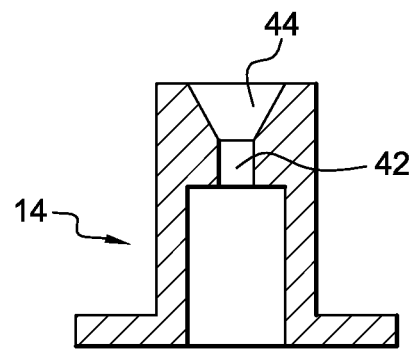
FIG. 1 is a diagrammatic view showing how the sealing member of an embodiment of a device of the invention operates.

The end-piece 10 includes a sealing member 14 disposed between a first portion 16 and a second portion 18 of the end-piece 10. Said sealing member 14, or sealing valve, can take up a liquid-blocking position or non-return or "check" position shown in FIGS. 2 and 3, in which position it prevents any liquid from returning once said liquid has left the sealed zone, and a liquid release position (not shown). Preferably, the member 14 is disposed in the vicinity of the distal end of the end-piece 10, in the vicinity of a liquid release orifice 64 (see FIG. 3). As can be seen in the diagrams of FIGS. 1 and 2, the sealing member 14 is provided with metering means 44, 46 for metering out the liquid to be dispensed, which means are described below.

The end-piece 10 is capped with a closure cap that is not shown in the figures.

The configuration of the end-piece 10 in a particular embodiment is described more precisely below, with reference to FIGS. 2 and 3. The example of FIG. 3 corresponds to a slight variant of the example of FIG. 2. In FIG. 2, the sealing member 14 is in two portions 34, 36 and is held in the blocking position by means of a return spring 15, whereas in FIG. 3, the member 14 is made entirely of an elastomer material and is held in the blocking position by deformation, as described below.

As shown in FIG. 2, the first portion 16 of the end-piece 10 is an inner core 16 provided with a protuberance 19 that is of substantially cylindrical shape and the projects from the distal end of the core 16. At its distal end, said protuberance 19 carries bearing means 20 for bearing against the sealing member 14. In this example, said bearing means 20 are composed of a projection forming an annular bead designed to bear against the sealing member 14. Alternatively, the bearing means 20 may be composed of the end of the protuberance 19 only, without including a projection on said end. The inner core 16 is also provided with a channel 22 for passing the liquid from the container towards the outside of the device, and with a connection portion for connecting the core 16 to the container 12. The end-piece 10 is also provided with vent means designed to pass air into the inside of the container so as to compensate for the volume of liquid flowing out. In this example, the vent means are carried by the inner core 16 and they comprise a channel 24 through which air can flow and across which a hydrophobic filter 26 is disposed that is designed to filter the incoming air without, however, enabling liquid to escape via the channel 24. More precisely, in this example, the filter 26 is disposed in a housing 28 for receiving the filter, which housing 28 is in the form of an annular groove disposed at the center of the inside surface of the core 16, and in which groove the filter 26 is embedded.

In this example, the second portion 18 of the end-piece 10 corresponds to an outer top casing of the end-piece 10. This outer casing 18 is designed to cap the inner core 16, the sealing member 14 (at least partially), and the spring 15. More precisely, it is provided with an open internal protuberance 30, formed by a central annular groove opening out into the orifice 64, and designed to surround the distal end of the protuberance 18 and the distal end of the sealing member 14 in such a manner as to make it possible for liquid to flow out of the device. The casing 18 is further provided with a bearing seat 32 for the return element 15, this seat 32 being disposed around the protuberance 30. In this example, the distal end of the member 14, via which end the liquid is delivered, projects slightly from the orifice 64. Provision could be made for this end to come flush with the surface of the orifice 64, or to be set back into the end-piece 10. Or else provision could be made for the end 14 to project further from the surface of the casing 18, thereby making it possible to isolate the drops more easily relative to the surface of the casing 18.

In this example, the sealing member is made up of an elastomer portion 34 and of a rigid portion 36, the portions 34 and 36 being constrained to move with each other, i.e. when the portion 34 moves, the portion 36 moves with it, and vice versa. In this example, the portions 34 and 36 are assembled together by overmolding, but other types of assembly could be considered. The elastomer portion 34 is made of an elastomer material, such as silicone or a thermoplastic elastomer. The rigid portion 36 is made of a plastics material such as polypropylene. The rigid portion 36 is provided with a bearing surface 38 for the return element 15. As can be seen in the figures, the rigid portion 36 covers the elastomer portion 34 over substantially the entire surface thereof, a zone 40 of the elastomer portion nevertheless being left free at the end of the elastomer portion, so as to enable said elastomer portion 34 to lengthen. More precisely, each of the portions, namely the elastomer portion 34 and the rigid portion 36, has the shape of a hat provided with a central cylindrical shape, of shape substantially complementary to the shape of the protuberance 19 of the core 16, this cylindrical shape being extended at its proximal end by a brim. Thus, the rigid portion 36 covers the elastomer portion 34 over a large fraction of its surface, except at its periphery 40. As can be seen in the figures, each of the portions 34, 36 defines a channel 42, provided in the end-wall of its cylindrical central shape, enabling the liquid to flow out. In addition, the sealing member 14 is provided with metering means 44, 46 for metering out the liquid to be dispensed, these means being means for forming drops of liquid. More precisely, said means are formed in the rigid portion 36 of the member 14. The means 44 have the shape of a cone starting from the channel 42 and flaring towards the distal end of the device, in such manner as to form a drop and to prevent the liquid being dispensed in a jet, the cone 44 opening out into a cylindrical portion 46 making it possible to calibrate the drop.

In this example, the return element 15 is a spiral metal spring. This element 15 exerts a return force on the sealing member 14, by bearing on the surface 38 of the rigid portion 36, in such a manner as to urge the sealing member 14 back into its liquid-blocking position.

As can be seen in the figures, the sealing member 14 is fastened between the two portions 16, 18 in leaktight manner, in order to prevent any liquid flowing through the channel 22 from escaping into the casing 18.

Operation of the dispenser device of FIG. 2 is described below.

When the user wishes to use the device, said user firstly removes the cap from the device. In order to dispense drops of liquid, the user actuates the device, thereby increasing the pressure inside the container, and causing liquid to flow into the channel 22, and thereby exerting pressure on the elastomer portion 34. Under this pressure, the sealing member goes from its liquid-blocking position to its liquid release position, by moving in translation upwards, as indicated by the arrow 48. More precisely, the zone 40 of the elastomer portion 34 deforms, by lengthening, so as to allow the elastomer portion to move upwards in this way. At the end of this movement, the sealing provided by the bearing means 20 co-operating with the sealing member 14 is broken, and the liquid can flow through the channel 42 and into the portions 44, 46, so as to form a drop of liquid. The path of the liquid is indicated by the arrow 50. Once the drop has been released, the user can cease to exert pressure on the container, which fills with air via the channel 24. In addition, since the pressure from the outgoing liquid ceases, the sealing member 14 resumes its liquid-blocking position, under the effect of the return force of the element 15. Thus, the bearing means 20 and the elastomer portion of the member 14 co-operate again so as to prevent liquid from flowing out. It should be noted that, in this blocking position, the member 14 blocks the liquid by compression of the portion 34 against the rigid portion 36, this compression being achieved by the means 20.

It should be noted that the example described can have variants. In particular, the return element 15 is a spiral spring, but it is possible to provide other types of return spring, made of metal or of some other material, such as a resilient blade or an elastomer element. In particular, said return element 15 may be incorporated directly into the sealing member 14 by being incorporated either into the elastomer portion 34 or into the rigid portion 36, or else it may be incorporated into the casing 18.

Among the advantages of the device of FIG. 2, it can be understood that, since the metering means 44, 46 are provided on the member 14, they are no longer close to the sealed zone, defined by the bearing of the means 20. In addition, since said metering means are disposed directly on the member 14, the risks of contamination by the liquid penetrating into the "dirty" portions (disposed downstream from the sealed zone) are much lower than if said metering means were disposed on a part that is not secured to or integral with the member 14, e.g. on the casing 18. It should be noted that, in the example of FIG. 2, the metering means are provided on the rigid portion 36, and this can be easier to implement and can procure more uniform metering than if they were provided on the elastomer portion 34. However, it is also possible to consider providing them on said elastomer portion 34.

Among the other advantages of the dispenser device in this example, it should be noted, in particular, that the rigid portion 36 constitutes a sort of shell for the elastomer portion 34, which shell makes it easier to exert stress on the sealing member 14, without any risk of deforming it.

In the variant of FIG. 3, the sealing member is an element that may be made of elastomer or of a plastics material that is sufficiently flexible, and that is made entirely of the same material, and the end-piece does not include any spring. In this example, the member 14 achieves the liquid-blocking by being mounted as deformed on the device. The member 14 is hat-shaped, provided with a cylindrical shape 65 and with a brim 66. The periphery 68 of this brim is fastened permanently between the portions 16 and 18, so as to provide static sealing. This fastening is achieved by deforming the member 14: said member 14 is fitted over the protuberance 19 and deformed in such a manner that the member 14 is constrained to press against the protuberance 19, and more precisely against the means 20. The shape of the member 14 shown in FIG. 3 is different from the shape of the member 14 prior to assembly. This pressing of the member 14 procures the sealing in the blocking position. Thus, in this example shown in FIG. 3, the member 14 blocks the liquid by bending deformation of the member 14, procured by the bearing means 20 disposed in register with a recessed zone.

In the example shown in FIG. 3, the metering means 44, 46 are provided entirely in the elastomer element 14. These means 44, 46 are analogous to the means of FIG. 2.

The device of FIG. 3 operates analogously to the device of FIG. 2.

It should be noted that the invention is not limited to the above-described examples.

What is claimed is:

1. A device for dispensing predetermined metered quantities of liquid, the device including an end-piece comprising a hat-shaped sealing member that can take up a liquid release position, allowing liquid to flow out of the device, and a non-return position preventing liquid from flowing back into the device, wherein:
   the end-piece further comprises an inner core and an outer top casing, the outer top casing having a top surface with an orifice for releasing liquid from the device;
   the sealing member, having a top portion with an outer sidewall, is fastened between the inner core and the outer top casing in a leak-tight manner to prevent any liquid from escaping into the outer casing, the outer top casing circumscribing and substantially covering the outer sidewall of the sealing member;
   the top portion of the sealing member comprises a liquid-passing channel and a flared shape opening that flares from and surrounds said channel, said flared shape opening defining a metering element for metering out the liquid to be dispensed, the metering element for forming drops of liquid; and
   the metering element is disposed in the immediate vicinity of the orifice in the top surface of the outer top casing for releasing the liquid from the device.

2. A device according to claim 1, including a bearing element for bearing against the sealing member, in register with a recessed zone, serving to deform the sealing member by bending deformation so that it takes up its non-return position.

3. A device according to claim 1, wherein the sealing member is flexible at least in part, and the device includes a bearing element for bearing against the sealing member, serving to deform the flexible portion of the sealing member by compression deformation so that it takes up its non-return position.

4. A device according to claim 1, wherein the flared shape opens out into a substantially cylindrical shape.

5. A device according to claim 1, wherein the sealing member is an elastomer element that is made entirely of elastomer.

6. A device according to claim 1, wherein the sealing member comprises an elastomer portion and a rigid portion, said portions being constrained to move with each other.

7. A device according to claim 6, wherein the metering element is formed in the rigid portion.

8. A device for dispensing predetermined metered quantities of liquid, comprising:
   an end-piece comprising a hat-shaped sealing member that can take up a liquid release position, allowing liquid to flow out of the device, and a non-return position preventing liquid from flowing back into the device;

said end-piece comprising an inner core and an outer top casing, the outer top casing including a top surface with an opening through which liquid is released from the sealing member and an internal protuberance with a central annular groove opening out into the opening;

the sealing member, including a top portion with an outer sidewall, being fastened between the inner core and the outer top casing in a leak-tight manner to prevent any liquid from escaping into the outer casing, wherein the internal protuberance circumscribes and substantially covers the outer sidewall of the sealing member; and the top portion of the sealing member comprising a liquid-passing channel and a cone shaped portion that flares from and surrounds said channel, said flared shape opening defining a metering element for metering out the liquid to be dispensed, wherein the metering element forms drops of liquid and the metering element is disposed in the immediate vicinity of the opening in the top surface of the outer top casing.

9. A device according to claim 8, wherein the cone shaped portion opens out into a substantially cylindrical shaped portion of the metering element.

10. A device according to claim 8, wherein the sealing member consists of an elastomer material.

11. A device according to claim 8, wherein the sealing member comprises an elastomer portion and a rigid portion constrained to move with each other.

12. A device according to claim 11, wherein the metering element is formed in the rigid portion.

* * * * *